(12) United States Patent
Kwon et al.

(10) Patent No.: US 6,413,537 B1
(45) Date of Patent: Jul. 2, 2002

(54) NYSTATIN FORMULATION HAVING REDUCED TOXICITY

(75) Inventors: Glen S. Kwon, Waunakee; Bong K. Yoo, Madison, both of WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/522,381

(22) Filed: Mar. 10, 2000

(51) Int. Cl.⁷ .............................. A61F 2/00; A61K 9/00; A61K 47/30

(52) U.S. Cl. .................... 424/423; 424/400; 514/772.2; 514/937; 514/975

(58) Field of Search .............................. 514/772.2, 937; 514/975; 424/241, 423

(56) References Cited

U.S. PATENT DOCUMENTS

| | | | |
|---|---|---|---|
| 4,006,222 A | | 2/1977 | Metzger |
| 4,082,881 A | * | 4/1978 | Chen et al. .................. 424/241 |
| 4,766,046 A | | 8/1988 | Abra et al. |
| 4,812,312 A | | 3/1989 | Lopez-Berestein et al. |
| 5,178,875 A | | 1/1993 | Lenk et al. |
| 5,281,420 A | | 1/1994 | Kelm et al. |
| 5,514,662 A | | 5/1996 | Seaman |
| 5,552,309 A | | 9/1996 | March |
| 5,696,298 A | | 12/1997 | Emanuele et al. |
| 5,733,873 A | | 3/1998 | Osterberg et al. |
| 5,756,552 A | * | 5/1998 | Takeuchi et al. ......... 514/772.2 |
| 5,776,904 A | | 7/1998 | Seki et al. |
| 5,811,088 A | | 9/1998 | Hunter et al. |
| 5,830,498 A | | 11/1998 | Lenk et al. |
| 5,834,472 A | | 11/1998 | Sangekar et al. |
| 5,874,104 A | | 2/1999 | Alder-Moore et al. |
| 5,955,427 A | | 9/1999 | McGregor et al. |

FOREIGN PATENT DOCUMENTS

| | | |
|---|---|---|
| FR | 2 782 455 | 2/2000 |
| GB | 809 105 | 2/1959 |
| WO | WO 00/47187 | 8/2000 |

OTHER PUBLICATIONS

Physicians Desk Reference "Mytrex" 54th Editing 2000.*
Martindale The Extra Pharmacopoeia "Nystatin", 1993.*
Alliance Pharmaceutical Corp., "About FloGel", http://www.allp.com/FloGel/fg_about.htm.
Alliance Pharmaceutical Corp., "FloGel Technology Overview" http://www.allp.com/FloGel/fg_ovr.htm, p. 1–2.
Barwicz, J., et al., "Effects of the Aggregation State of Amphotericin B on Its Toxicity to Mice", *Antimicrobial Agents and Chemotherapy*, Oct. 1992 p. 2310–2315.
Cameron, P., ed. *Good Pharmaceutical Freeze–Drying Practice* Illinois; Interpharm Press, Inc. 1997.
Forster, D., et al., "Toxicity of Solubilized and Colloidal Amphotericin B Formulations to Human Erythrocytes", *J. Pharm. Pharmacol.*, 1998 40: 325–328.
Hazen, E., and Brown, R., "Fungicidin, an Antibiotic Produced by Soil Actinomycete", *Proc. Soc. E. Biol. Med.* 1951 76, 93–97.
Legrand, P., et al., "Effects of Aggregation and Solvent on the Toxicity of Amphotericin B to Human Erythrocytes", *Antimicrobial Agents and Chemotherapy*, Nov. 1992 p. 2518–2522.

(List continued on next page.)

Primary Examiner—James M. Spear
Assistant Examiner—Blessing Fubara
(74) Attorney, Agent, or Firm—Michael Best & Friedrich LLP; Teresa J. Welch; Jill A. Fahrlander (57) ABSTRACT

The present invention provides a novel formulation of nystatin for parenteral administration to treat systemic fungal infections. The formulation avoids the toxicity and solubility problems of prior art nystatin formulations.

19 Claims, 7 Drawing Sheets

OTHER PUBLICATIONS

Wallace, T., et al., "Activity of Liposomal Nystatin against Disseminated", *Aspergillus fumigatus* Infection in Neutropenic Mice, *Antimicrobial Agents and Chemotherapy*, Oct. 1997 p. 2238–2243.

Yamashita, K., et al., Micelle/Monomer "Control over the Membrane–Disrupting Properties of an Amphiphilic Antibiotic", *J. Am. Chem. Soc.*, 1995, 117, p. 6249–6253.

* cited by examiner

NYSTATIN FORMULATION HAVING REDUCED TOXICITY

STATEMENT REGARDING FEDERALLY SPONSORED RESEARCH OR DEVELOPMENT

This invention was made with U.S. Government support under Grant No. 1 R29 AI43346-01 awarded by the National Institutes of Health. The U.S. Government has certain rights in this invention.

CROSS-REFERENCE TO RELATED APPLICATIONS

Not applicable.

BACKGROUND OF THE INVENTION

The present invention relates to the antifungal drug nystatin, and, in particular, a novel parenteral formulation of nystatin which avoids the side adverse effects associated with parenteral administration of known nystatin formulations.

Nystatin is an intracellular product first isolated from *Streptomyces noursei*. Nystatin is a polyene antibiotic, having a large, conjugated double bond ring system linked to a mycosamine (a 3-amino-3,6-dideoxy-D-manno-pyranose) moiety, an epoxy group, and an all-trans tetraene system. Its structure is similar to erythromycin and amphotericin B, other macrocyclic lactones. Its empirical formula is $C_{47}H_{75}NO_{17}$ and molecular weight is 926.13. Nystatin is only slightly soluble in water.

Nystatin has been found to inhibit the growth of a variety of pathogenic and non-pathogenic yeast and fungi, and to be effective in treating histoplasmosis and cryptococcosis (E. Hazen and R. Brown, *Proc. Soc. Exp. Biol. Med.* 1951, 76, 93–97). Nystatin is both fungistatic and fungicidal in vitro against a wide variety of yeasts and fungi. It has dependable efficacy for treatment of cutaneous, oral and intestinal infections caused by *Candida albicans* and other Candida species. Nystatin exhibits no appreciable activity toward bacteria, protozoa or viruses.

Nystatin and other polyene macrolides are known to act at the cell membrane level by binding to sterols and forming pores in the membrane that lead to cell death. The selectivity of nystatin for fungal cells over mammalian cells appears to be due to preferred binding to ergosterol, the primary fungal sterol, over mammalian cholesterol.

Nystatin is well tolerated in both oral and topical forms, and is generally administered as an ointment, an oral suspension, an oral tablet, and a vaginal tablet. Nystatin USP contains not less than 5000 units of nystatin activity per mg. Nystatin is available as oral tablets of 500,000 units per tablet, and as an ointment of 100,000 units/g ointment.

Recently, nystatin has been used to treat systemic fungal infections in immunocompromised patients, although it is too toxic for parenteral use. Systemic administration of polyene macrolides such as nystatin can cause serious side effects such as hemolytic toxicity and nephrotoxicity. Because of its high toxicity and insolubility in water, nystatin is thus not commercially available in parenteral formulations. These properties have generally precluded its use for systemic infection.

The toxicity of nystatin for parenteral administration appears to be related to its low solubility. Nystatin forms aggregates in water, and aggregated species are correlated with increased toxicity toward mammalian cells in vitro and in vivo. Detergents have been suggested as deaggregating agents. However, the high levels of detergent typically required to reduce formation of aggregates also result in high toxicity.

Some prior art has suggested that these problems could be overcome by formulating nystatin in phopholipid vesicles or liposomes (See, e.g., U.S. Pat. No. 4,812,312 issued to Lopez-Bernstein, et al.; U.S. Pat. No. 5,874,104 issued to Alder-Moore, et al.). An improved liposomal formulation is disclosed in U.S. Pat. No. 5,830,498 issued to Lenk, et al. Liposomes, however, are difficult to prepare reproducibly in bulk and can be unstable. Others have suggested that liquid dispersion forms can be administered parenterally (See, e.g., U.S. Pat. No. 5,776,904 issued to Seki et al.). Such dispersion forms also suffer from stability problems.

Notwithstanding the known problems with parenteral use of nystatin, the art has not adequately responded to date with a formulation of nystatin suitable for the treatment of systemic fungal infections that is relatively easy to prepare and has a lower toxicity for parenteral administration than nystatin alone while still maintaining adequate efficacy.

SUMMARY OF THE INVENTION

The present invention provides a formulation of nystatin in lyophilized, solid dispersion form which is readily reconstituted with water to be suitable for parenteral administration. The novel formulation is less toxic and more soluble in water than conventional nystatin formulations while maintaining adequate antifungal properties.

The foregoing and other advantages of the present invention are realized in one aspect thereof in a formulation comprising a solid dispersion which is a lyophilized homogeneous mixture that includes, by weight, 1% to 10% nystatin, 10 to 98% dispersing agent, 0 to 1% co-solvent and water. The dispersing agents are surface active agents that are suitably nonionic block copolymers of ethylene oxide and propylene oxide, generically referred to as poloxamers, e.g., poloxamer 407, poloxamer 188, or suitably sorbitan esters, generally polysorbates, e.g., polysorbate 80. The dispersing agent is present in an amount effective to reduce aggregate formation of nystatin in an aqueous solution. The co-solvent is suitably a polar organic solvent that is present in the formulation in an amount effective to increase solubility of nystatin in water. Preferably, the co-solvent is selected from the group consisting of dimethylsulfoxide, dimethylacetamide, dimethylformamide and methanol. Optionally, other inert excipients are suitably present in the formulation.

In another aspect, the present invention provides a method for preparing the nystatin formulation. The method includes the steps of (a) dissolving nystatin in an aqueous solution of a dispersing agent and a co-solvent, (b) sonicating the solution of step (a) to promote a substantially homogeneous dispersion, and (c) freeze-drying the dispersion of step (b) to form a solid dispersion. Preferably, the solid dispersion thus formed remains stable for long periods of time, suitably several months. The solid dispersion in lyophilized form or powder is suitably reconstituted with an aqueous solvent, preferably water or saline, to form a nystatin solution suitable for parenteral administration to a subject, e.g., a human or animal, in need thereof.

In yet another aspect, the present invention provides a composition comprising a solid dispersion formulation of nystatin and a sterile aqueous vehicle. Preferably, the composition includes nystatin at a concentration from about 100 $\mu$M to about 1000 $\mu$M.

In a further aspect, the present invention provides a method of treating a fungal infection in a human or animal subject which includes the step of administering to the human or animal in need thereof an antifungally effective amount of the nystatin composition in accordance with the present invention.

Other advantages and a fuller appreciation of the specific attributes of the invention will be gained upon an examination of the following drawings, detailed description of preferred embodiments, and appended claims.

DESCRIPTION OF A PREFERRED EMBODIMENT

The present invention relates to a novel freeze-dried or lyophilized formulation of nystatin (Nys) that can be reconstituted to form a solution suitable for parenteral administration to a human or animal. The present invention provides a nystatin formulation that retains the antifungal properties of nystatin, but has reduced toxicity and increased solubility relative to solutions of nystatin in water. These attributes are achieved through a novel combination of physical and chemical features.

In the following description of the method of the invention, process steps are carried out at room temperature and atmospheric pressure unless otherwise specified. As used herein, the terms "sonicate" or "sonicating" refer to treating a sample with ultrasonic energy. The terms "deaggregated" or "deaggregation" refer to non-aggregated, monomeric or reduced aggregated forms of nystatin or the process of making these forms. "Nonionic surfactant" refers to a surfactant which lacks net ionic charge and does not dissociate to an appreciable extent in aqueous media. The properties of nonionic surfactants are largely dependent upon the proportions of the hydrophilic and hydrophobic groups in the molecule. "Solid dispersion" refers to a solid medium with the components thereof substantially uniformly dispersed therein. "Lyophilization" refers to the process whereby a substance is prepared in dry form, e.g., powder or thin film, by rapid freezing and dehydration and evaporation.

The formulation in accordance with the present invention is a solid dispersion prepared from an aqueous solution that includes a dispersing agent, a co-solvent, and nystatin. Nystatin USP is a non-sterile yellow to light tan powder, commercially available from, e.g., Paddock Laboratories or Geneva Generics.

Nonionic copolymer surfactants are suitable dispersing agents in accordance with the present invention. An especially favorable aspect of the present invention is the use of block copolymers of ethylene oxide and propylene oxide, generically referred to as poloxamers, as dispersing agents. Poloxamers improve the solubility of nystatin in the present formulation. Poloxamers are a series of nonionic surfactants represented by the structure wherein the polyoxypropylene segment, $(C_3H_6O)_b$, is hydrophobic and the polyoxyethylene segments, $(C_2H_4O)_a$, are hydrophilic. Preferable are those poloxamers wherein a is an integer ranging from about 50 to 100, more preferably 75 to 98, and b is an integer ranging from about 20 to 70, more preferably 30 to 67. Such poloxamers are commerically available under the trademark Pluronic from BASF Corporation of Mount Olive, N.J. Specifically, poloxamer 188 (Pluronic F68®) and poloxamer 407 (Pluronic F127®) are useful. Other poloxamers which may be of value in the present invention are poloxamer 237 (Pluronic F87®), poloxamer 238 (Pluronic F88®), poloxamer 288 (Pluronic F98®), and poloxamer 338 (Pluronic F108®). These poloxamers in accordance with the present invention have a molecular weight in the range of about 6600 daltons to about 14,000 daltons and a melting point in the range of about 49° C. to about 57° C.

The preferred Pluronic F68® has a molecular weight of 8,400 g/mole, and a melting point of 52° C. Pluronic F68® has an average of 75 units of ethylene oxide (A block), 30 units of propylene oxide (B block), and 75 units ethylene oxide (A block). The preferred Pluronic F127® has a molecular weight of 12,600 g/mole, and a melting point of 56° C. It has an average of 98 units of ethylene oxide (A block), 67 units of propylene oxide (B block) and 98 units of ethylene oxide (A block). Preferably, the molar ratio of nystatin to Pluronic F127® in the present formulation ranges from about 1:10 to about 2:1. The molar ratio of nystatin to Pluronic F68® suitably ranges from about 1:100 to about 2:1.

Other preferred surfactants or dispersing agents in accordance with the present invention are polyoxyethylene sorbitan fatty acid esters which include polysorbates such as polysorbate 80, polysorbate 20, polysorbate 40 and polysorbate 60 and other sorbitan esters such as sorbitan monolaurate, sorbitan monooleate, sorbitan monopalmitate and sorbitan monostearate. Preferred is polysorbate 80 (sorbitan mono-9-octadecanoate) which is suitably present in the formulation with nystatin in molar concentrations ranging from about 0.1 mM to about 100 mM. The molar ratio of nystatin to polysorbate 80 suitably ranges from about 1:2 to 1:100. Polysorbates are commercially available from ICI Americas, Inc., Wilmington, Del., U.S., under the Tween trademark. Polysorbate 80 is available as Tween 80®.

An additional component in the formulation in accordance with the present invention is a co-solvent, which is any suitable water-soluble substance compatible with the formulation that dissolves nystatin, preferably a polar organic solvent, for example, dimethylsulfoxide (DMSO), dimethylacetamide (DMAC), dimethylformamide (DMF) and methanol.

Optionally, excipients may be added to the water-based formulation, for example, a lyoprotectant such as sucrose or mannitol, and/or an antioxidant such as butylated hydroxyanisole.

The nystatin formulation of the present invention, especially when prepared by the method described herein, provides a solid dispersion with increased solubility and decreased toxicity with no significant loss in antifungal activity when compared to nystatin alone.

The method in accordance with the present invention includes, dissolving nystatin in a co-solvent and a dispersing agent, sonicating the resulting solution at appropriate temperature and frequency to form a substantially homogeneous dispersion, freeze-drying the dispersion to form a lyophilized form or solid dispersion, and reconstituting the lyophilized form under suitable conditions for use. Specifically, the method includes the steps of dissolving nystatin in an aqueous solution of the dispersing agent, e.g., Pluronic 127®, and a co-solvent, e.g., dimethylsulfoxide (DMSO). The resulting solution is heated, and then sonicated at a frequency of about 45 KHz using conventional sonication equipment for a period of time sufficient to provide a substantially homogeneous dispersion. The heating temperature suitably ranges from about 4° C. to about 60° C., depending on the time period for heating. Preferably, the solution is heated at a temperature of about 37° C. for a time period of about 10 minutes. Following sonication, the substantially homogeneous dispersion is freeze-dried in accordance with conventional procedures, for example, as described in Peter Cameron ed. Good Pharmaceutical Freeze-Drying Practice (Illinois; Interpharm Press, Inc. 1997), which is incorporated by reference. The dispersion may be frozen at a low temperature with or without excipients such as a lyoprotectant. Preferably, the dispersion is frozen at a temperature below −40° C. Vacuum may be utilized to extract water and co-solvent from the dispersion to concentrate the product. It is envisioned that other means of evaporation may be employed, including spray drying the formulation at an elevated temperature to drive off the water and solvent.

A typical formulation of preferred components before freeze-drying is shown as follows:

|  | % W/V (range) |
|---|---|
| Nystatin | 0.1–10% |
| Dispersing agent, e.g., Pluronic F127 ® | 1.0–10% |
| Co-solvent, e.g., Dimethylsulfoxide | 0.1–10% (v/v) |
| Sterile water | (remainder to volume) |

Upon freeze-drying or lyophilization, the solid dispersion is in an amorphous state which is a stable powder. The solid dispersion typically includes, by weight, about 1% to about 10% nystatin, about 10% to about 98% dispersing agent, 0 to about 1% co-solvent and water. The solid dispersion readily undergoes dissolution compared to the powder form of nystatin, which undergoes slow dissolution. The solid dispersion may be stored below room temperature, suitably 2° C.–8° C., preferably less than 4° C., for extended periods of time, generally several months.

The freeze-dried or lyophilized nystatin formulation is suitably reconstituted in a sterile aqueous vehicle such as sterilized water, water for injection (USP) or saline, to form an antifungal solution suitable for parenteral administration. Typically, the concentration of nystatin in a reconstituted solution is about 100 $\mu$M to about 1000 $\mu$M. The reconstituted nystatin formulation of the present invention retains antifungal activity and has reduced toxicity relative to a nystatin preparation made by dissolving nystatin in water or saline.

The nystatin formulation prepared by the method of the present invention not only has reduced toxicity and increased solubility, but also is deaggregated when compared with nystatin in water or saline, or nystatin simply mixed with the dispersing agent and co-solvent. The deaggregation property, as noted previously, is important in light of the fact that nystatin easily forms aggregates in water which appear to be responsible for the toxicity toward mammalian cells in vitro and in vivo. The antifungal activity of the formulation is the same as or increased relative to that of nystatin in water or saline. The present method provides an increase in the therapeutic index of nystatin.

The nystatin formulation of the present invention is suitably used to treat a number of fungal infections in humans and animals. The nystatin formulation may be administered by conventional techniques, but is preferably administered parenterally such as by intravenous infusion or by intravenous, subcutaneous or intramuscular injection. Typically, a daily dosage of the nystatin in accordance with the present invention is about 1.0 mg/day/kg of body weight to about 10 mg/day/kg of body weight. Specific doses of nystatin for each particular patient, of course, depend on a wide variety of factors, for example, on age, body weight, general state of health, sex, diet, timing of administration, rate of excretion, medications used in combination, and the severity of the disease or condition to be treated.

The present invention is further explained by the following examples which are illustrative, and should not be construed by way of limiting the scope of the present invention.

EXAMPLE 1

Preparation of Freeze-dried Nystatin Formulations (NF)

Nystatin formulations were prepared in the molar ratios listed below in Table 1. For each formulation, an appropriate amount of nystatin USP was dissolved into 0.50 mL of dimethylacetamide (DMAC) under light protection. An aliquot (0.35 mL) of this solution was taken and added into 10 mL of a 5% Pluronic F127® solution. After mixing thoroughly, the solution was sonicated for 10 min at a frequency of 45 KHz and 30° C., and then frozen quickly by using liquid nitrogen or a dry ice chamber. Water and DMAC were evaporated under high vacuum and very low temperature (−70° C., freeze-drier recommended) for at least 24 hrs. The various formulations and their characteristics are shown below in Table 1.

TABLE 1

| | Freeze-dried nystatin formulations (NF) | | | | |
|---|---|---|---|---|---|
| molar ratio (Nys:Pluronic) | Nys content (% w/w) | input Nys content (% w/w) | yeild* (%) | Solubility (mg/mL) | 50% hemolysis inducing level of Nys ($\mu$g/mL) 127) |
| NF (2:1) | 9.49 | 12.81 | 74.1 | 1.3 | 120 |
| NF (1:1) | 6.00 | 6.85 | 87.6 | 0.9 | 120 |
| NF (1:2) | 3.43 | 3.54 | 96.9 | 1.4 | 180 |

TABLE 1-continued

Freeze-dried nystatin formulations (NF)

| molar ratio (Nys:Pluronic) | Nys content (% w/w) | input Nys content (% w/w) | yeild* (%) | Solubility (mg/mL) | 50% hemolysis inducing level of Nys ($\mu$g/mL) 127) |
|---|---|---|---|---|---|
| NF (1:4) | 1.77 | 1.80 | 98.3 | >2.0 | 170 |
| pure Nys | — | — | — | 0.54 | 60 |

*yield = 100 × Nys contents/input Nys contents

EXAMPLE 2:
Measurement of Critical Aggregation Concentration (CAC) of Nystatin in Distilled Water Containing Pluronic F127®

Figure 6:
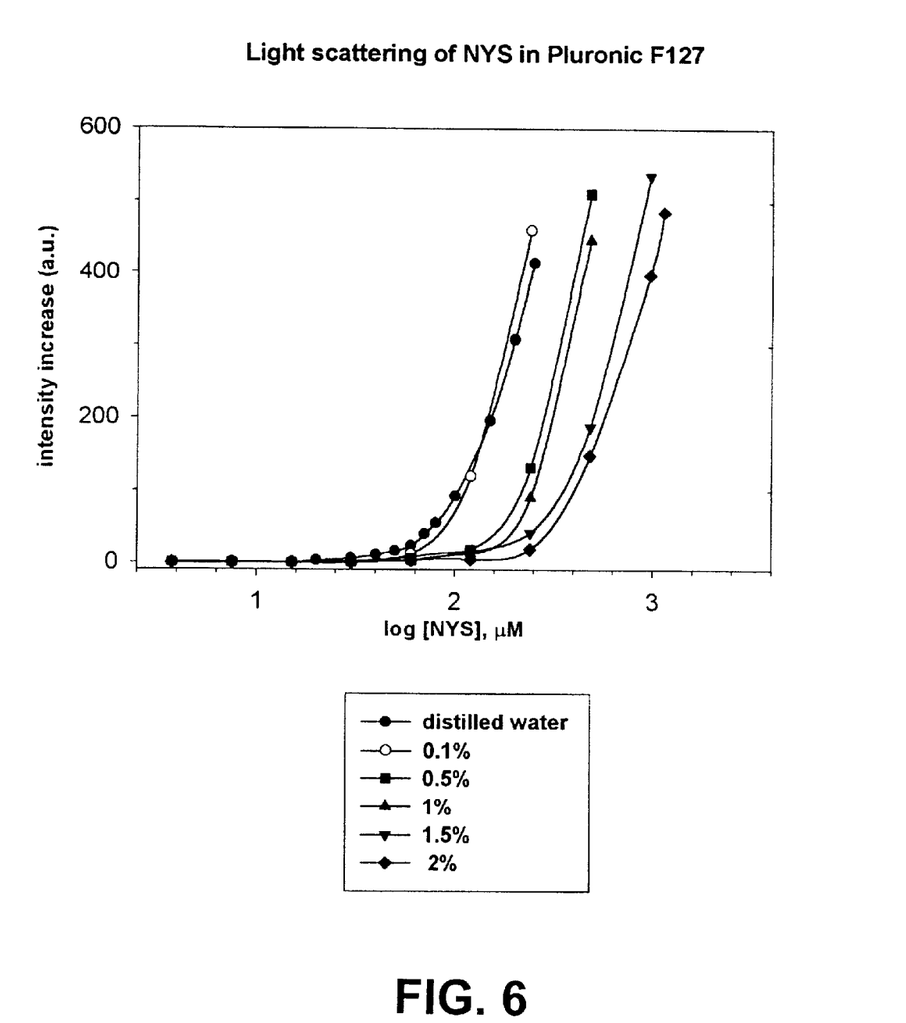
FIG. 6 is a graph showing the results of the light scattering of nystatin in Pluronic F127®.

Nystatin (16 mg) was dissolved into 0.3 mL of dimethylsulfoxide (DMSO) under light protection, and was added into 15 mL of various aqueous Pluronic F127® solutions ranging from 0.1%–2.0%, making a 1100 $\mu$M nystatin solution. Each solution was serially diluted with the corresponding Pluronic F127® solution until a 3.8 $\mu$M nystatin concentration was obtained. After incubation at 37° C. for 30 min, each solution was subjected to light scattering using fluorimeter with fixed excitation wavelength of 450 nm. Band widths for excitation and emission were set at 3 nm and 1.5 nm, respectively. The intensity of scattered light was plotted as a function of logarithmic concentration of nystatin as seen in FIG. 6. The intersection point of two linear lines was defined as the critical aggregation concentration (CAC) where self-aggregation of nystatin molecules begins, leading to an abrupt increase of intensity of scattered light. The calculated CAC is given in Table 2 below.

TABLE 2

Critical aggregation concentrations (CAC) of nystatin in distilled water containing varied levels of Pluronic F127 ®

| % Pluronic F127 ® | 0.1% | 0.5% | 1.0% | 1.5% | 2.0% |
|---|---|---|---|---|---|
| CAC ($\mu$M) | 50.1 | 108.0 | 134.2 | 154.3 | 217.9 |

The CAC in distilled water alone is 52.8 $\mu$M.

These results show that use of the poloxamer raises the CAC in a concentration-dependent manner. The poloxamer can deaggregate nystatin into a monomeric, highly deaggregated form which is non-toxic but active against fungal cells. Thus, the nystatin formulation in accordance with the present invention has lower toxicity as demonstrated by reduced aggregation measured by the intensity of scattered light.

EXAMPLE 3
Monomerizing Effect of Various Surfactants

The monomerizing or light scattering effects of various surfactants, sodium deoxycholate (NaDC) and sodium lauryl sulfate (SLS), were compared to the preferred surfactants. Nystatin formulations were prepared with various surfactants similar to the method of Example 1. The concentration of drug was kept constant at 200 $\mu$M. The intensity of the scattered light was measured using a fluorimeter with a fixed excitation wavelength of 450 mm. The results of conventional light scattering tests are shown in FIG. 7.

Figure 7:
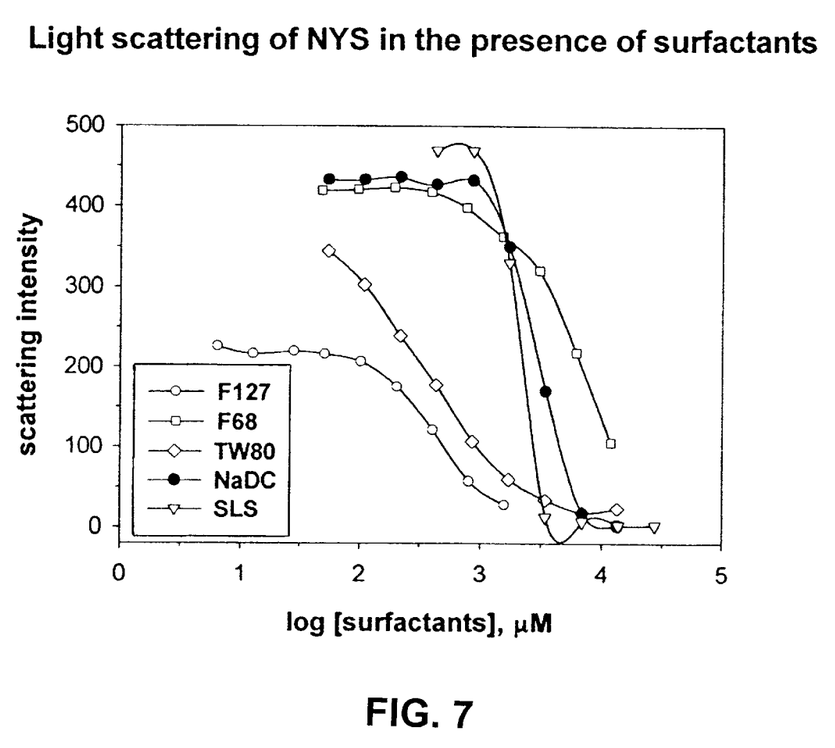
FIG. 7 is a graph showing the results of the light scattering of nystatin in various surfactants.

As seen in FIG. 7, as the level of surfactant increases, light scattering intensity dramatically decreases. Pluronic F127® and Tween 80® show a deaggregating activity at about 100 $\mu$M compared to about 1000 $\mu$M of the other surfactants tested.

EXAMPLE 4
Solubility Measurement of Freeze-dried Nystatin Formulations (NF)

An excess amount of each NF formulation from Example 1 was placed into 0.5 mL of distilled water, and mixed vigorously for 5 min with a vortex mixer. After filtering the slurry with a 0.45 $\mu$m syringe filter, the filtrate was diluted with dimethylformamide (DMF) for analysis. The amount of nystatin in each NF composition was calculated by absorption spectroscopy at 307 nm.

The solubility results are shown in Table 1. These results demonstrate that the solubility of nystatin prepared as a solid dispersion with Pluronic F127® in accordance with the present invention has greater solubility than that of pure nystatin (e.g., a 1:4 nystatin-Pluronic F127 formulation has a solubility >2 mg/mL compared to 0.5 mg/mL for pure nystatin). The increase in solubility is due to Pluronic F127® and the method in accordance with the present invention used to prepare the solid dispersion.

EXAMPLE 5
Hemolysis Testing

To test the hemolytic properties of nystatin in Pluronic F127®, concentrated erythrocytes (red blood cells) were diluted into an isotonic phosphate buffer solution (PBS), having a pH of 7.0 and containing Pluronic F127® in concentration ranges from 0.1% to 2.0%. Nystatin solutions were prepared by dissolving 70 mg of nystatin into 2 mL of DMSO until the solution became clear, forming a first nystatin stock solution. 0.2 mL of this first stock solution was then added to 5 mL of each of the Pluronic F127®/PBS solutions to form a second nystatin stock solution. Various amounts of the second stock solution were added to the Pluronic F127®/PBS solutions of varied levels of nystatin.

Aliquots (2.5 mL) of diluted erythrocytes containing varied levels of nystatin were shaken gently to make homogeneous. The solutions were then incubated at 37° C. and shaken at 200 strokes/min. for 30 min. Unlysed erythrocytes were removed by centrifugation (12,000 g, 20 sec). The supernatant was collected and, using absorption spectroscopy, analyzed for hemoglobin at 576 nm. The percent lysed erythrocytes was determined using the following equation: % hemolysis=$100(Abs-Abs_o)/(Abs_{100}-Abs_o)$. Abs, $Abs_o$ and $Abs_{100}$ stand for the absorbances for the sample, the control with no nystatin, and the control in the presence of 20 $\mu$g/mL amphotericin B, respectively. The results are shown in FIG. 4.

Figure 4:
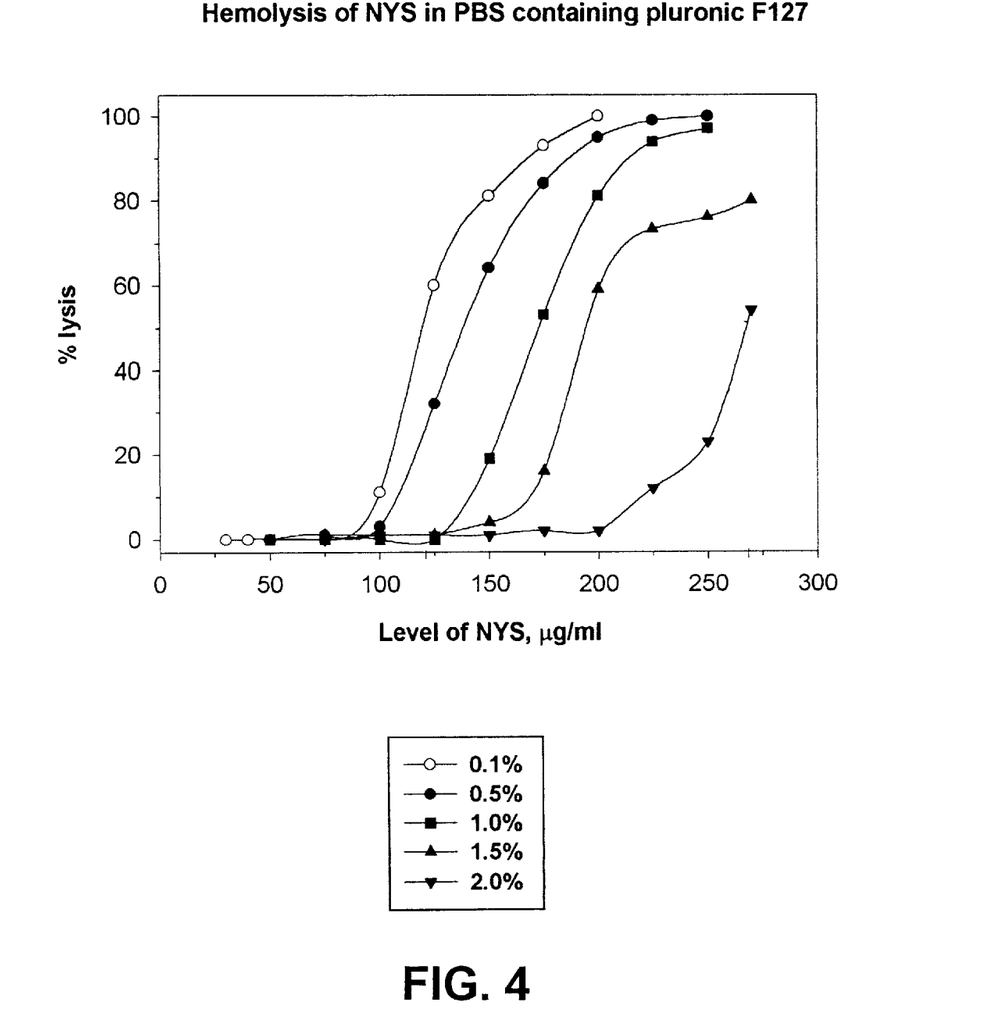
FIG. 4 is a graph showing the hemolytic activity of nystatin/Pluronic F127® in PBS as a function of nystatin concentration.

As seen in FIG. 4, the concentration of nystatin causing 50% hemolysis increases with increasing Pluronic F127® concentration (e.g.,~120 $\mu$g/mL at 0.1% Pluronic F127® compared to ~270 $\mu$g/mL at 2% Pluronic F127®).

Figure 5:
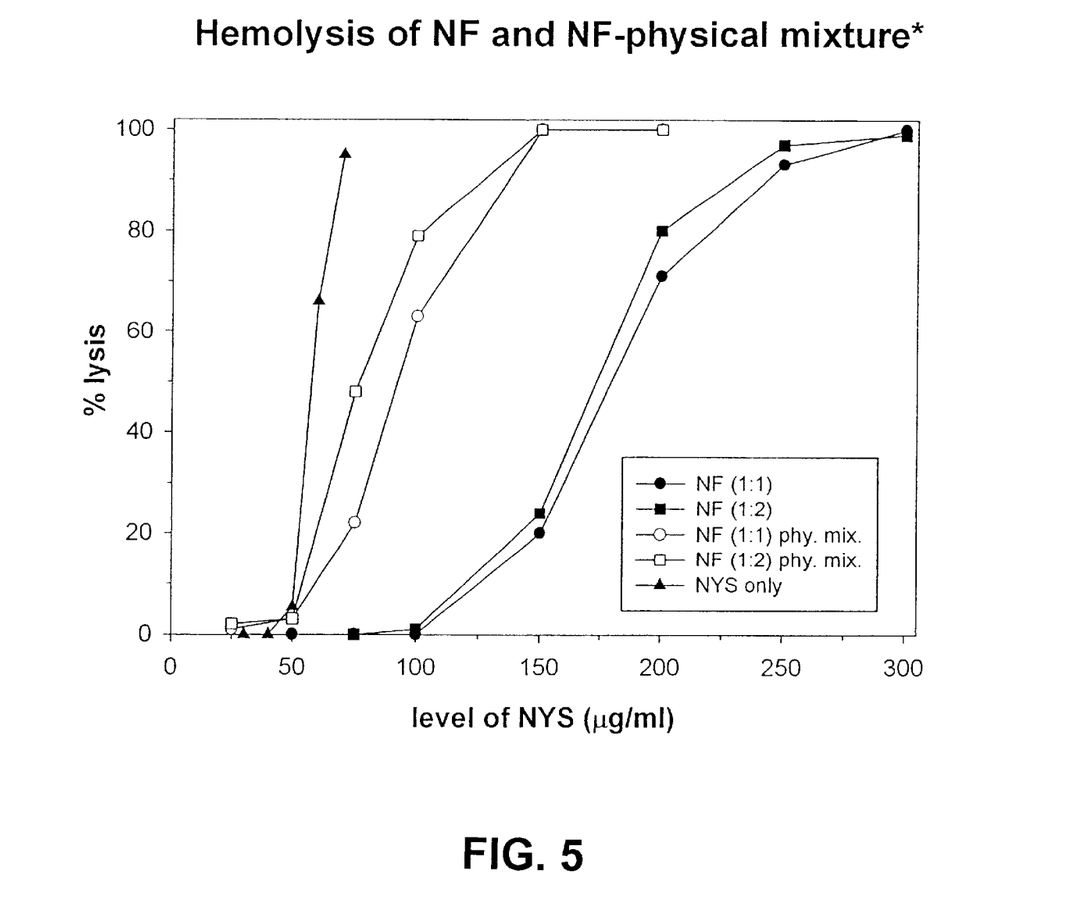
FIG. 5 is a graph showing the comparative hemolytic activity of a physical mixture of nystatin/Pluronic F127®, nystatin formulations (NF) and nystatin alone in accordance with the present invention.

The hemolytic activity of NF compositions (1:2) and (1:1) in accordance with the present invention was also compared to that of a physical mixture of nystatin with Pluronic F127® and that of nystatin alone. Erythrocytes were diluted into isotonic PBS alone, mixed with the NF compositions, pure nystatin or physical mixtures of nystatin and Pluronic F127® (no incubation and freeze drying) and processed as described above. The results are shown in FIG. 5. FIG. 5 demonstrates that in physical mixtures, nystatin causes 50% hemolysis at a level of about 75–90 µg/mL. Nystatin prepared as a solid dispersion with Pluronic F127® in accordance with the present invention, i.e., the NF compositions, causes 50% hemolysis at about 175–180 µg/mL.

Figure 3:
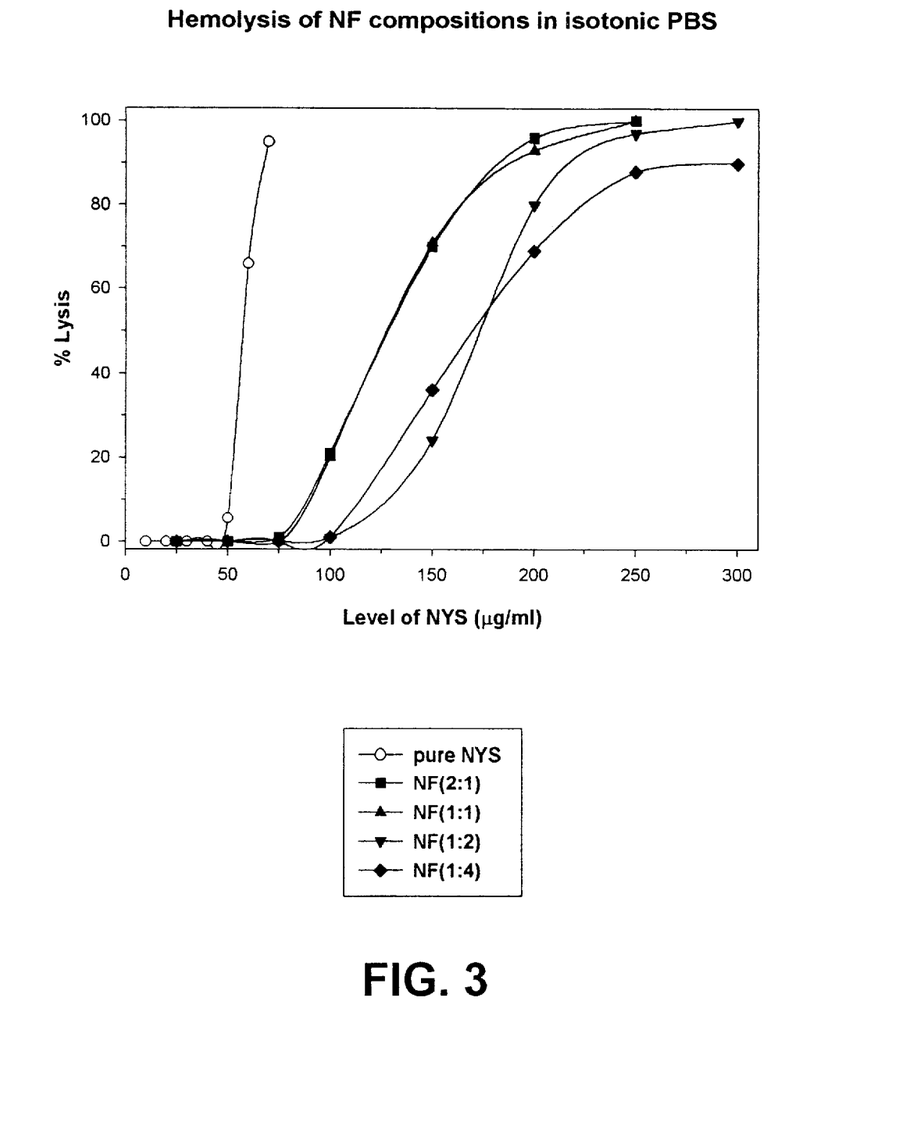
FIG. 3 is a graph showing the hemolytic activity of nystatin formulations (NF) and nystatin alone in isotonic PBS.

By similar procedure, the hemolytic activity of the NF compositions in accordance with the present invention was further compared with that of nystatin in isotonic PBS solutions. The results are shown in FIG. 3. FIG. 3 illustrates that pure nystatin causes 50% hemolysis at about 55 µg/mL. The NF compositions cause 50% hemolysis at much higher concentrations, ranging from about 125 µg/mL to about 175 µg/mL.

The foregoing results demonstrate that the nystatin formulation in accordance with the present invention has lower toxicity than simple physical mixtures of nystatin and poloxamer or nystatin alone as measured by reduced lysis of red blood cells.

Figure 1:
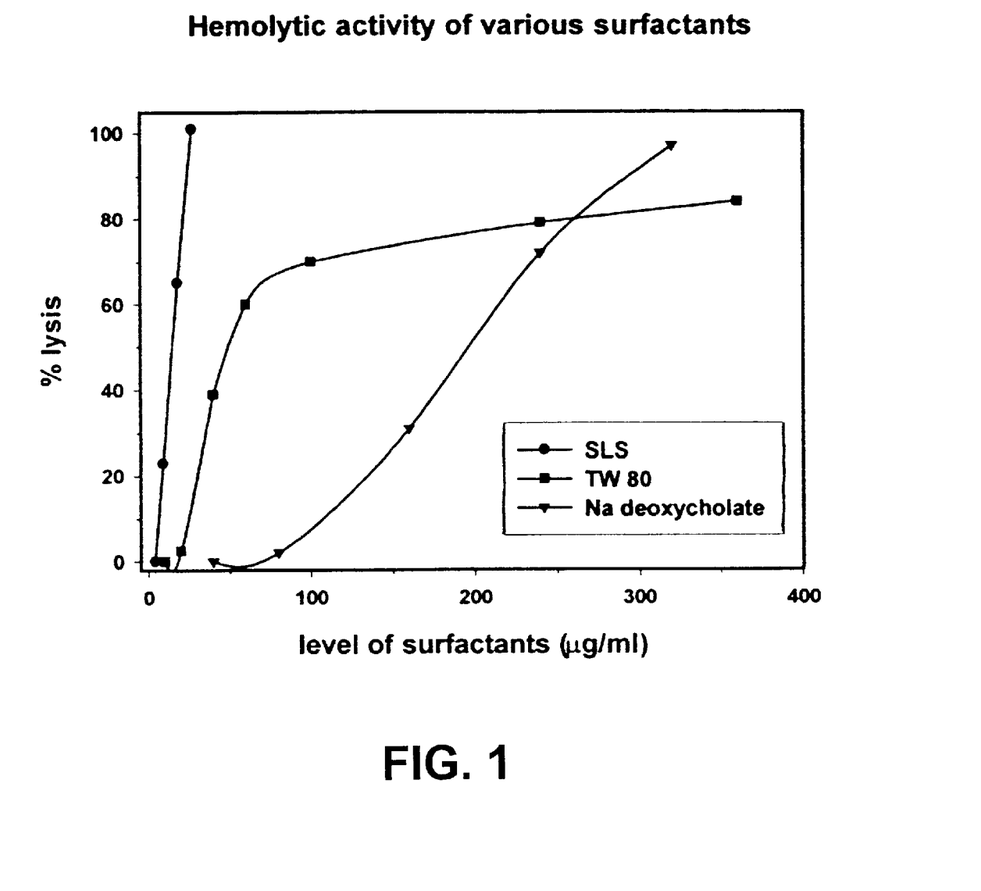
FIG. 1 is a graph showing the hemolytic activity of various surfactants alone.
Figure 2:
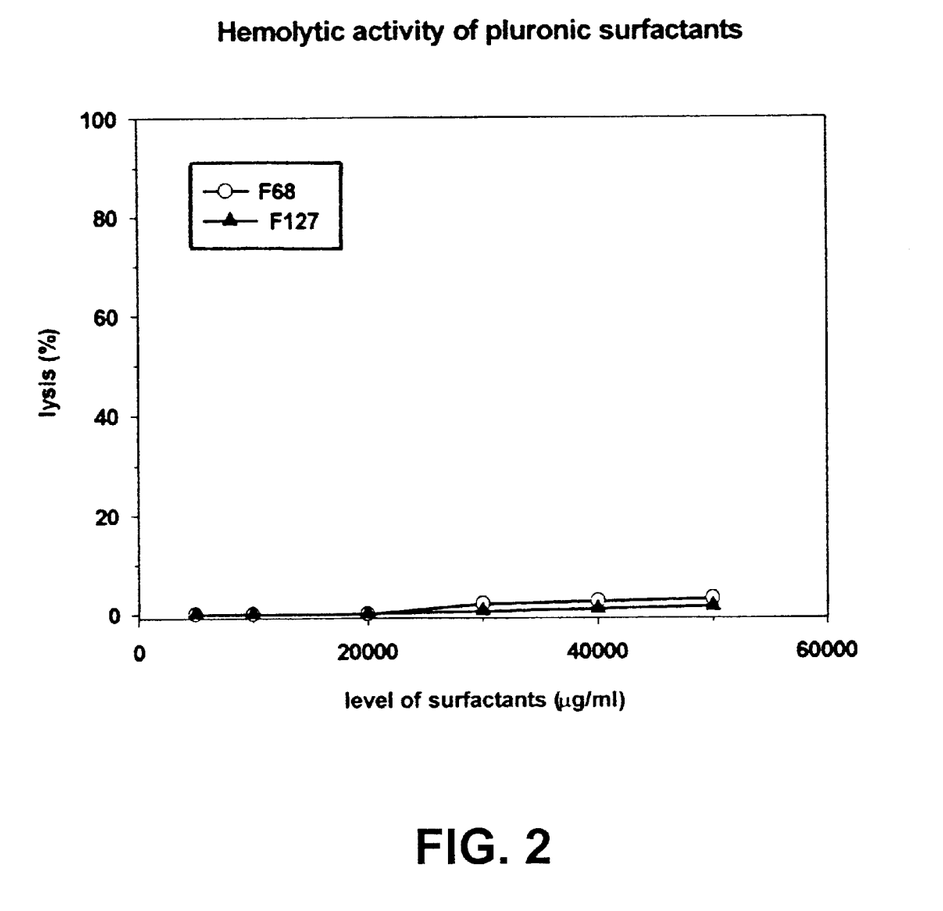
FIG. 2 is a graph showing the hemolytic activity of Pluronic F68® and Pluronic F127®.

The hemolytic activity of various surfactants alone was also determined and the results are shown in FIGS. 1 and 2, respectively. FIG. 1 shows the % hemolysis of the surfactants, sodium lauryl sulfate (SLS), Tween 80® and NaDC (sodium deoxycholate). As shown in FIG. 1, SLS and Tween 80® cause 50% hemolysis at concentrations less than 50 µg/mL, while NADC causes 50% hemolysis at about 200 µg/mL. FIG. 2 shows the % hemolysis of the preferred surfactants, Pluronic F68® (F68) and Pluronic F127® (F127). As demonstrated in FIG. 2, these surfactants caused virtually no hemolysis.

EXAMPLE 6
Minimal Inhibitory Concentration (MIC) of NF Compositions

NF samples were dissolved into DMSO and diluted with Bacto® YPD broth medium (10 g of Bacto® YPD in 200 mL of distilled water, and sterilized at 121° C.–124° C.), to give a nystatin level of 8 µg/mL. Nystatin levels were varied by serial dilution with broth medium to a level of 0.1 µg/mL. An aliquot (800 µL) of each nystatin sample was put into a microcentrifuge tube. 50 µL of the inoculum, containing $5 \times 10^3$ cfu/mL of *Saccharomyces cerevisiae*, ATCC 4921, in sterile distilled water, was added to each tube to give a total volume of 850 µL per tube. The tubes were incubated at 30° C. for 24 hr. A solvent control, Pluronic F127® control, and medium control were performed simultaneously to check the growth inhibiting activities of DMSO and Pluronic F127® as well as the sterility of the broth medium. The minimal inhibitory concentration (MIC) was defined as the minimum concentration of nystatin that showed a full inhibition of *Saccharomyces cerevisiae* in the tube, examined by measuring the optical density at 600 nm. The MIC for the nystatin formulations in accordance with the present invention was determined to be 3 µg/mL. The MIC of nystatin alone for *Saccharomyces cerevisiae* is about 3 µg/mL.

EXAMPLE 7
Minimal Fungicidal Concentration (MFC) of Nystatin Formulations (NF)

For measurement of minimal fungicidal concentration (MFC), the same procedure as the MIC measurement was employed up to the incubation step. Tubes containing *Saccharomyces cerevisiae* were placed in an incubator at 37° C. for 2 hrs., so that the cells might be killed. After 2 hrs. contact with the sample, the surviving cells were precipitated on the bottom of the tube by centrifugation (12000 g, 20 sec), and the supernatant decanted. The cells were washed with 1 mL of sterile distilled water and vortex mixed. 0.1 mL of the mixed cells was spread evenly on a YPD agar plate and incubated at 30° C. for 24 hr, Thereafter, the colonies of *Saccharomyces cerevisiae* were counted and the concentration showing no colony on the agar plate was defined as the MFC. All experiments were repeated three times. The MFC for the compositions in accordance with the present invention was determined to be 3 µg/mL. The MFC for nystatin alone is 12 µg/mL.

EXAMPLE 8
In vivo Testing

A group of mice infected with *Candida albicans* is intravenously inoculated five hours after infection with a single dose of a reconstituted solution of a nystatin formulation in accordance with the present invention in sterile water. Another group of mice infected with *Candida albicans* is intravenously inoculated five hours after infection with a nystatin USP solution in DMSO and diluted with saline. The results show that a significantly higher number of mice are protected from death by the dose of nystatin formulation than those given nystatin USP solution.

In summary, the present invention provides a novel formulation of nystatin for parenteral administration to treat systemic fungal infections. The formulation avoids the toxicity and solubility problems of prior art nystatin formulations. The nystatin formulation in accordance with the present invention has a lower toxicity as measured by, e.g., reduced lysis of red blood cells in vitro, has reduced aggregation in solution as measured by light scattering determinations, e.g., a critical aggregation concentration (CAC) greater than that of nystatin alone in water, and has increased solubility in aqueous solution compared to nystatin alone, e.g., a solubility greater than 0.54 mg/mL. At the same time, the formulation maintains antifungal activity the same or greater than nystatin alone as measured by, e.g., a minimal inhibitory concentration (MIC) equal to that of nystatin alone and a minimal fungicidal concentration (MFC) less than that of nystatin alone.

While the present invention has now been described and exemplified with some specificity, those skilled in the art will appreciate the various modifications, including variations, additions and omissions, that may be made in what has been described. Accordingly, it is intended that these modification also be encompassed by the present invention and that the scope of the present invention be limited solely by the broadest interpretation that lawfully can be accorded the appended claims.

We claim:

1. An antifungal composition comprising a lyophilized solid dispersion which includes, by weight, about 1% to about 10% nystatin, about 10% to about 98% of at least one dispersing agent selected from the group consisting of poloxamers and polysorbates, and 0 to 1% of a co-solvent.

2. The formulation of claim 1 wherein the dispersing agent is selected from the group consisting of poloxamer 407, poloxamer 188, and polysorbate 80.

3. The formulation of claim 1 wherein the co-solvent is selected from the group consisting of dimethylsulfoxide, dimethylacetamide, dimethylformamide and methanol.

4. The formulation of claim 1 wherein the molar ratio of nystatin to dispersing agent ranges from about 1:100 to about 2:1.

5. A pharmaceutical formulation suitable for intravenous, subcutaneous or intramuscular injection comprising a lyophilized nystatin solid dispersion and a pharmaceutically acceptable carrier, the lyophilized nystatin dispersion comprising nystatin and a dispersing agent.

6. The pharmaceutical formulation of claim 5 wherein the nystatin is present at a concentration of about 100 μM to about 1000 μM.

7. The pharmaceutical formulation of claim 5 wherein the dispersing agent is selected from the group consisting of poloxamer 407, poloxamer 188 and polysorbate 80.

8. A method of preparing a solid dispersion of nystatin and a dispersing agent, comprising:

(a) dissolving nystatin in an aqueous solution of a dispersing agent and a co-solvent;

(b) sonicating the solution of step (a) at a temperature and at a frequency for a period of time sufficient to form a substantially homogenous dispersion; and (c) freeze-drying the dispersion of step (b) to form a solid dispersion of nystatin and dispersing agent.

9. The method of claim 8 wherein the dispersing agent is selected from the group consisting of poloxamer 407, poloxamer 188, and polysorbate 80.

10. The method of claim 8 wherein the co-solvent is selected from the group consisting of dimethylsulfoxide, dimethylacetamide, dimethylformamide and methanol.

11. A method of preparing a parenteral formulation of nystatin, the formulation having increased solubility and reduced toxicity relative to a nystatin composition prepared by suspending nystatin in water, comprising reconstituting a solid dispersion prepared by the method of claim 8 with a suitable aqueous vehicle.

12. A nystatin composition comprising a fungicidally effective amount of a lyophilized nystatin formulation and a pharmaceutically acceptable carrier, the nystatin formulation including nystatin and a dispersing agent, the molar ratio of nystatin to dispersing agent being about 1:100 to about 2:1, the composition having: reduced aggregation relative to that of nystatin dissolved in water, as measured by light scattering; and having lower toxicity relative to that of nystatin dispersed in an isotonic saline solution as measured by reduced lysis of red blood cells in vitro.

13. A method of treating a fungal infection in an animal, comprising the step of administering to the animal a fungicidally effective amount of a nystatin composition of claim 12.

14. The method of claim 13 wherein the composition is administered at a dosage of nystatin about 1 mg/day/kg of body weight to 10 mg/day/kg of body weight.

15. The method of claim 13 wherein the nystatin composition is administered parenterally.

16. An antifungal composition comprising a solid dispersion which includes, by weight, about 1% to about 10% nystatin, about 10% to about 98% of at least one dispersing agent selected from the group consisting of poloxamers and polysorbates, and 0 to 1% of a co-solvent.

17. The formulation of claim 16 wherein the dispersing agent is selected from the group consisting of poloxamer 407, poloxamer 188, and polysorbate 80.

18. A pharmaceutical formulation suitable for intravenous, subcutaneous or intramuscular injection comprising a solid dispersion and a pharmaceutically acceptable carrier, the solid dispersion comprising nystatin and a dispersing agent selected from the group consisting of poloxamers and polysorbates.

19. The formulation of claim 18, wherein the solid dispersion comprises, by weight, about 1% to about 10% nystatin, about 10% to about 98% of at least one dispersing agent selected from the group consisting of poloxamers and polysorbates, and 0% to 1% of a co-solvent.

* * * * *